US009108001B2

(12) United States Patent
Plumptre

(10) Patent No.: US 9,108,001 B2
(45) Date of Patent: Aug. 18, 2015

(54) DRUG DELIVERY DEVICE WITH PISTON ROD CARRYING DOSE MARKINGS

(75) Inventor: David Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/141,080

(22) PCT Filed: Dec. 21, 2009

(86) PCT No.: PCT/EP2009/067616
§ 371 (c)(1),
(2), (4) Date: Oct. 21, 2011

(87) PCT Pub. No.: WO2010/072702
PCT Pub. Date: Jul. 1, 2010

(65) Prior Publication Data
US 2012/0046613 A1   Feb. 23, 2012

(30) Foreign Application Priority Data

Dec. 23, 2008   (EP) .................................... 08022334

(51) Int. Cl.
*A61M 5/315* (2006.01)
*A61M 5/24* (2006.01)
*A61M 5/31* (2006.01)

(52) U.S. Cl.
CPC ....... *A61M 5/31511* (2013.01); *A61M 5/31525* (2013.01); *A61M 5/24* (2013.01); *A61M 2005/2407* (2013.01); *A61M 2005/3125* (2013.01); *A61M 2005/3126* (2013.01); *A61M 2005/3142* (2013.01)

(58) Field of Classification Search
CPC ..................... A61M 5/31511; A61M 5/31525; A61M 5/24; A61M 2005/2407; A61M 2005/3125; A61M 2005/3126; A61M 2005/3142
USPC .......................................... 604/181, 189, 207
See application file for complete search history.

(56) References Cited

U.S. PATENT DOCUMENTS

| 2,736,315 | A | * | 2/1956 | Feeney ......................... 604/211 |
| 3,905,366 | A | * | 9/1975 | Callahan et al. ............... 604/209 |
| 5,092,842 | A | * | 3/1992 | Bechtold et al. ............... 604/135 |
| 5,807,323 | A | * | 9/1998 | Kriesel et al. .................... 604/89 |
| 7,468,203 | B2 | * | 12/2008 | Hicks et al. .................... 428/141 |
| 2004/0116875 | A1 | * | 6/2004 | Fischer et al. ................. 604/227 |
| 2007/0244444 | A1 | * | 10/2007 | Guelker et al. ................ 604/207 |

FOREIGN PATENT DOCUMENTS

WO          02070050 A1    9/2002

OTHER PUBLICATIONS

Form PCT/IB/326, Notification Concerning Transmittal of International Preliminary Report on Patentability.

* cited by examiner

*Primary Examiner* — Theodore Stigell
*Assistant Examiner* — Lauren M Peng
(74) *Attorney, Agent, or Firm* — McDonnell Boehnen Hulbert & Berghoff LLP

(57) ABSTRACT

The present invention relates to a drug delivery (5) comprising a housing (10) with a proximal end (30) and a distal end (22), a cartridge holder (14) adapted to retain a cartridge (16), the cartridge holder (14) comprising an at least partially transparent side wall (36), a piston rod (26), the piston rod (26) being adapted to drive a piston so as to engage the piston (28) into the cartridge (16), and
a plurality of symbols (32) on the piston rod (26), the symbols (32) representing dosage information during operation of the drug delivery device (5) and being visible through a window aperture (40) in the housing (10) or in the cartridge holder (14). Furthermore, using a plurality of symbols (32) on a piston rod (26) to represent dosage information during operation of the drug delivery device (5) is disclosed.

17 Claims, 2 Drawing Sheets

DRUG DELIVERY DEVICE WITH PISTON ROD CARRYING DOSE MARKINGS

CROSS REFERENCE TO RELATED APPLICATIONS

Figure 1:
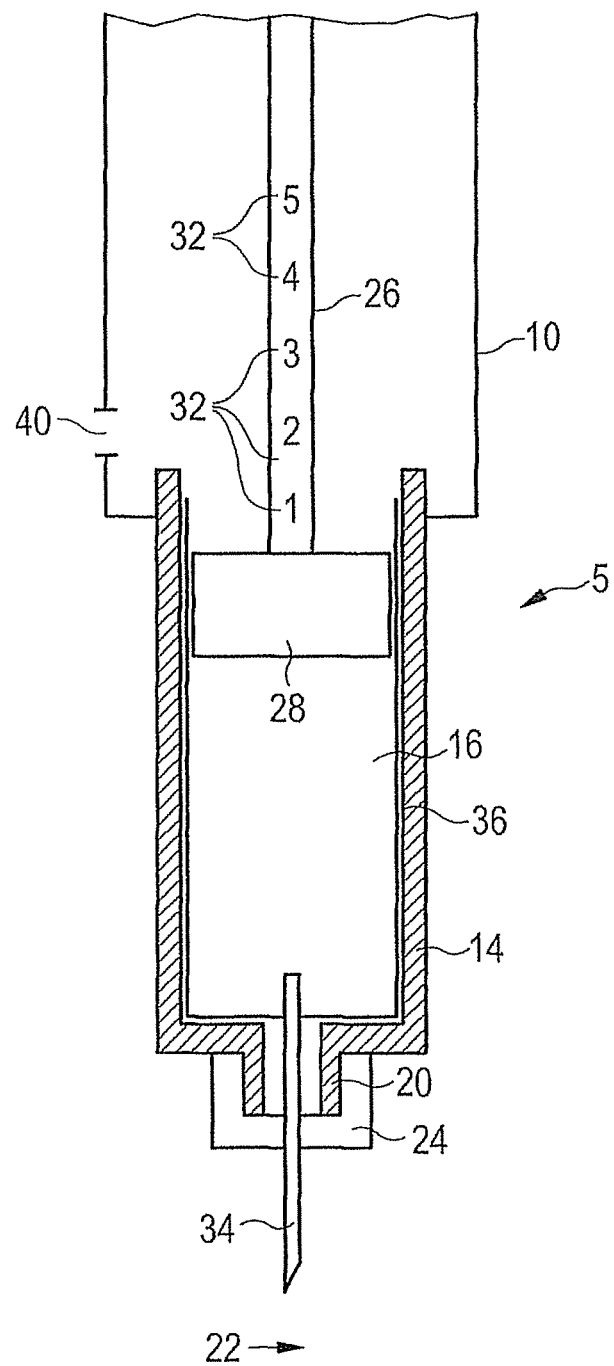

The present application is a 35 U.S.C. 371 National Application of PCT/EP2009/067616 filed Dec. 21, 2009 and claims priority to European Patent Application No. 08022334.0, filed Dec. 23, 2008, the entire contents of which are incorporated entirely herein by reference.

The present invention relates to drug delivery devices. Furthermore, the present invention relates to using a plurality of symbols on a piston rod to represent dosage information during operation of the drug delivery device.

Drug delivery devices are generally known for the administration of a medicinal product, for example insulin, growth hormones or other drugs, in particular medicinal products being suitable for self-administration by a patient.

Some drug delivery devices are configured to deliver a plurality of doses. One particular example of such a drug delivery device is described in the document EP 1 923 084 A1. There, a drug delivery device is shown where a user may activate the drug delivery device. The drug delivery device includes a drive mechanism suitable for use in pen-type injectors, wherein a number of pre-set doses of medicinal product can be administered. A needle unit can be attached to the drug delivery device for dispensing the medicinal product into a patient's skin. After usage of the drug delivery device, the distal end of the device can be covered by a cap.

Additionally, some drug delivery devices are configured to allow setting of different dose sizes which are to be delivered.

It is generally advisable that the user is aware of the amount of medicinal product which is left in an injection device.

In EP 1 666 080 A1 an injection device is shown. The device has signal generators which are connected to operative elements of the device and which give off signals which represent the operative condition of the device. The signals are sent to an electronic circuit which controls a presentation of the operational condition of the device and presents operational conditions. The number of signals from each generator is counted and a number of operations exceeding a pre-set number for the signal generator in question are interpreted as representing a not allowed operational condition.

In US 2001/0053894 A1 a dose display for a medicine administration device is shown, in which rotation of a dose setting actuator is transmitted to a display means comprising a flexible disc carrying numbers in a band along its perimeter, which numbers are in accordance with the set dose presented in a window in a wall of the device to show said dose. During its rotation the disc is deflected to follow an inner contour of the device to attain a cylindrical shape.

In WO 2004/020028 A1 a device for the display of a dosage setting on an injection device is shown having a read-out region in the housing for the injection device and a graduated strip arranged within the housing. The graduated strip is at least partly run through the read-out region by means of a guide device. The graduated strip may be adjusted to correspond to a dosage setting for the injection device and the dosage setting may be read in the read-out region. A transport device for transporting the graduated strip past the read-out region is provided. The transport device is coupled to a dosage setting device on the injection device.

It is an aim of the present invention to provide for an improved drug delivery device. In particular, a drug delivery device should be provided, which allows for improved operability with respect to administered doses.

For this aim, a drug delivery device comprises a housing with a proximal end and a distal end, a cartridge holder adapted to retain a cartridge, the cartridge holder being secured to the housing and having an at least partially transparent side wall. The device further comprises a piston rod, the piston rod being adapted to drive a piston so as to engage the piston into the cartridge, and a plurality of symbols on the piston rod, the symbols representing dosage information during operation of the drug delivery device and being visible through a window aperture in the housing or in the cartridge holder.

When the drug is dispensed from the drug delivery device, the piston progressively moves forward towards the distal end of the cartridge. Through the window aperture in the housing, at least a respective one of the plurality of symbols on the piston rod is framed by the window aperture and is visible for the user. As the symbols represent dosage information during operation of the drug delivery device, the filling status of the drug delivery device can be easily recognized by viewing the information provided on the piston rod through the window aperture. This allows a user to quickly gain information regarding the drug delivery device.

Furthermore, providing the plurality of symbols on the piston rod does not add any additional components to the drug delivery device and is therefore a cost efficient and viable way of obtaining a dose counter. As virtually all pen-type drug delivery devices include a piston rod of some specific form, the inventive concept can be applied to any drug delivery device irrespective of the precise form of the piston rod.

In a first embodiment, the at least partially transparent side wall of the cartridge holder comprises a structured surface capable of unevenly reflecting light so as to at least partially render the symbols of the piston rod unreadable. The structured surface may be configured to be capable of unevenly reflecting light so as to at least partially render the symbols of the piston rod unreadable.

According to this embodiment, the symbols of the piston rod are rendered unreadable due to the structured surface of the cartridge holder by unevenly reflecting light passing through the side wall. The cartridge holder, in particular the at least partially transparent side wall of the cartridge holder, may be unitary. The cartridge holder, in particular the at least partially transparent side wall of the cartridge holder, may be formed from a translucent or transparent material, preferably just a single material, capable of providing the structured surface of the cartridge holder so as to at least partially render the symbols of the piston rod unreadable. As the piston progressively advances towards the distal end of the cartridge, the symbols would otherwise also be visible through the at least partially transparent side wall of the cartridge holder, in particular in addition to the window aperture in the housing. Hence, potential confusion of the user could occur which is largely eliminated in this embodiment. Consequently, operability of the drug delivery device is enhanced as the user can only view dosage related information on the piston rod through the window aperture.

In a further embodiment, the structured surface of the at least partially transparent side wall is arranged on the inner surface of the cartridge holder.

According to this embodiment, the surface of the cartridge holder for unevenly reflecting light is located on the inner side. Hence, the outer surface can be designed with almost no constraint regarding visual or ergonomic appearance. In addition, it is also possible to provide a graduated scale on the outer surface of the cartridge holder in a non-obscure way.

In one embodiment, the structured surface of the at least partially transparent side wall comprises a plurality of facets.

In this example, the structured surface of the transparent side wall is formed by facets which allows for a simple and cost efficient implementation of the structured surface capable of unevenly reflecting light. In addition, it is conceivable that the facets are arranged in a regular or irregular pattern on the inner surface of the cartridge holder. As such, the inner surface can be designed in many different ways without placing too many constraints for the manufacturer and requiring only a low precision during manufacturing.

In one embodiment, the structured surface of the at least partially transparent side wall comprises a plurality of undulating elements.

According to this embodiment, the structured surface of transparent side wall is formed by undulating elements which allows for a simple and cost efficient implementation of the structured surface by allowing many different ways of possible designs.

According to a further embodiment, the structured surface of the at least partially transparent side wall is capable of retaining the piston visible during engagement in the cartridge.

In this example, the regulatory requirement of allowing the user to view the position of piston during engagement in the cartridge can be simultaneously fulfilled with rendering the plurality of symbols unreadable. This allows the user to gather relevant information about the drug delivery device in a direct and non-confusing manner.

In a further embodiment, the structured surface of the at least partially transparent side wall comprises features being orientated along a horizontal axis between the proximal end and the distal end.

According to this embodiment, a flat end face of the piston is arranged perpendicular to the axis of the light reflecting or refracting elements, which allows the user to view the position of the piston unaltered. Consequently, the position of the piston can be determined with high accuracy by the user and without obscuring any graduated scale printed on the cartridge holder.

In a further embodiment, the plurality of symbols comprises consecutive numbers so as to indicate delivered dose or remaining dose left in the cartridge.

According to this embodiment, the user can directly derive dosage information. Hence, operability of the drug delivery device is enhanced as the user can gain key information in a simple manner, which may be related to e.g. imminent emptiness of the cartridge contained in the drug delivery device.

In a further embodiment, the numbers are printed or moulded on the piston rod.

In this example, the numbers related to dosage information can be provided already during manufacturing of the piston rod, e.g. by injection moulding, printing or the like. This reduces the number of necessary manufacturing steps and thus may lead to a reduction in manufacturing costs.

In a further embodiment, the cartridge holder comprises additional information suitable for providing further information to a user.

According to this embodiment, additional information directly attached to the cartridge holder can be viewed by the user so as to gain further information regarding the content of the cartridge or associated with the prescription of the medicinal product, for example. Usually, the cartridge itself is labeled according to its content. The structured surface, however, reduces the legibility of the information provided on the cartridge. Hence, the user may be more attracted to read the additional information directly attached to the cartridge holder. Accordingly, information is presented in a clearer, i.e. less visually confusing way.

In a further embodiment, the housing or the cartridge holder comprises two window apertures. The window apertures may be arranged oppositely with respect to each other. The window apertures may be arranged axially offset from each other. One of the window apertures may be arranged to display the symbols provided on the piston rod. The other one of the window apertures may be arranged to provide additional information provided by the cartridge holder. In a further embodiment, the other one of the window apertures may be arranged to display the cartridge, in particular the content of the cartridge. For this purpose, the window aperture may be formed by a section of the at least partially transparent side wall which does not comprise the previously described structured surface.

In a further embodiment, the piston rod is a linearly movable piston rod.

In this example, a conventional technique for providing a dosage mechanism in drug delivery devices may be employed. Using conventional techniques usually reduces costs and thus provides a cost-efficient drug delivery device. This is in particular useful when employing the drug delivery device as an expendable product.

In a further embodiment, the piston rod is a rotationally movable piston rod with a lead screw.

In this example, another conventional technique for providing a dosage mechanism in drug delivery devices may be employed so as to provide a cost-efficient drug delivery device.

In a further embodiment, the structured surface of the at least partially transparent side wall covers the upper part of the cartridge holder facing the proximal end.

According to this embodiment, the lower part of the cartridge holder facing the distal end of the device can allow a user to view the information printed on the cartridge. Usually, cartridges can be labeled according to their content. Consequently, the risk of a potential misuse of the drug delivery device is significantly reduced especially when the patient is required to apply different medicinal products.

According to a further embodiment, the window aperture is located near the proximal end of the cartridge.

In this example, the window aperture provides a framing of the displayed information such that the region close to the piston is visible as long as no medicinal product has been dispensed. Hence, the symbols can be attached to the piston rod starting from a position close to its distal end up to a position which is reached after the device is fully dispensed. Accordingly, dosage information can be provided over the entire range of dosage delivery.

According to a further embodiment, the cartridge holder may be provided as a piece separate from the housing. The cartridge holder can then be secured to the housing during assembly of the drug delivery device.

In addition, a cartridge holder may be employed such that the proximal end of the cartridge holder is arranged close to the proximal end of the cartridge.

The information represented on the piston rod referring to the first couple of doses dispensed will in many cases be located near the proximal end of the cartridge, since this location marks the starting position of a bung being advanced within the cartridge during dose delivery.

Thus, in the above mentioned case, the starting position of the bung will be also located near the proximal end of the cartridge holder.

In order to allow for the entire range of dosage information being provided to the user, it is desirable that the window aperture is located in close proximity to the cartridge holder.

According to a further embodiment, the cartridge holder and the housing may be formed unitarily.

According to another embodiment of the device, the side wall of the cartridge holder comprises an opaque part. However, not the complete side wall is opaque but there is provided at least one window aperture through which the piston rod is visible.

Furthermore, the piston rod is not rotated as it drives the piston during dose delivery.

The arrangement of the symbols on the piston rod, e.g. their angular position with respect to the axis of the piston rod is chosen such that they are covered by the opaque part of the side wall of the cartridge holder and are thus not visible through the window aperture in the cartridge holder.

As an example, the symbols are arranged linearly, e.g. in parallel to the axis of the piston rod.

According to a preferred embodiment, regarding the longitudinal axis of the piston rod the angular position of the window aperture of side wall of the cartridge holder is offset with respect to the angular position of the window aperture in the housing such that the angular regions visible through the respective window aperture do not interfere.

In order to provide for a sufficiently large visible angular region for each window aperture it is desirable to define the angular offset between the apertures in a range between 80 degree and 180 degree. In particular, a range between 80 degree and 100 degree is preferred.

For the above mentioned aim, a plurality of symbols is used on a piston rod to represent dosage information during operation of the drug delivery device by being visible through a window aperture in the housing, wherein the symbols on a piston rod are rendered at least partially unreadable through an at least partially transparent side wall of a cartridge holder.

Other features will become apparent from the following detailed description when considered in conjunction with the accompanying drawings.

Figure 2:
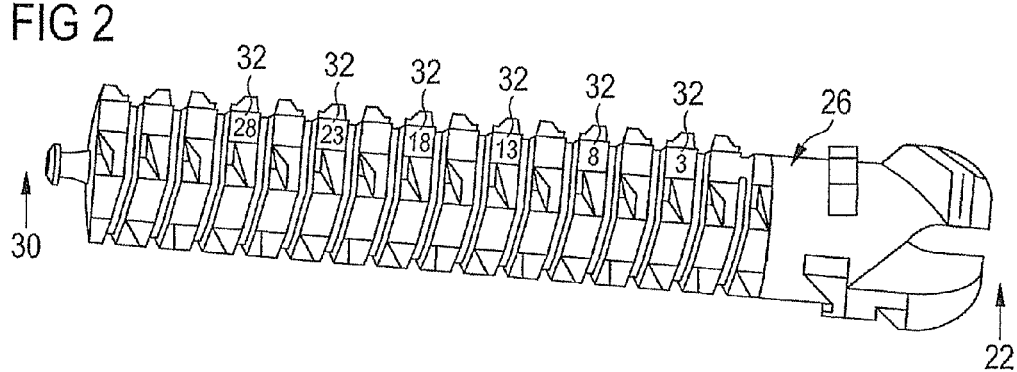
Figure 3A:
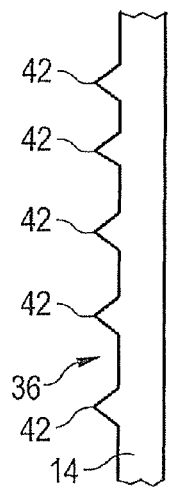
Figure 3B:
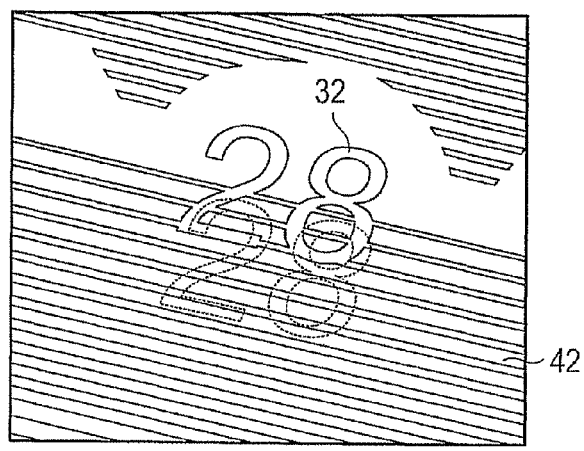
Figure 4:
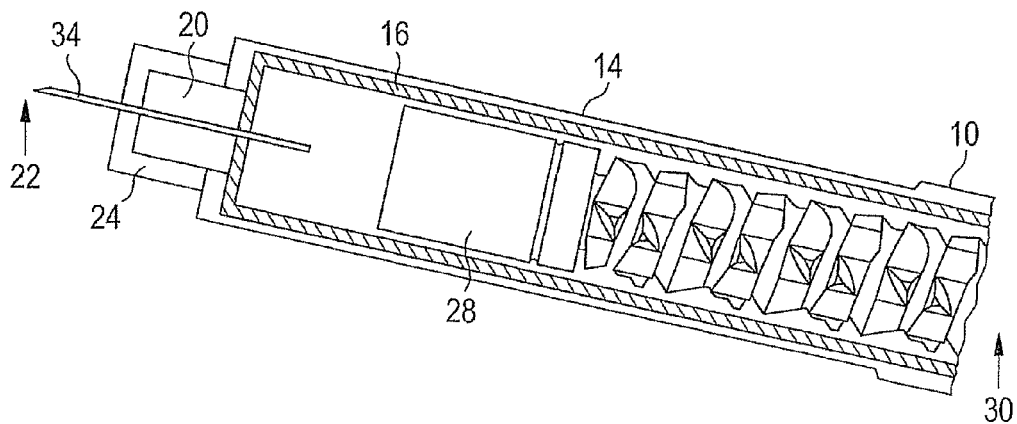

In the drawings:

FIG. 1 schematically shows a simplified cross sectional side view of a drug delivery device according to an embodiment;

FIG. 2 schematically shows a simplified side view of a part of a drug delivery device according to an embodiment;

FIG. 3A schematically shows a simplified cross sectional side view of a part of a drug delivery device according to an embodiment; and FIG. 3B schematically shows a simplified top view of a part of a drug delivery device according to an embodiment; and FIG. 4 schematically shows a simplified side view of a part of a drug delivery device according to an embodiment.

In FIG. 1 an embodiment of a drug delivery device 5 is shown, which is an injector for a liquid medication.

It should be noted that the description of the drug delivery device 5 as shown in FIG. 1 is merely illustrative.

The drug delivery device 5 may be configured to deliver a plurality of fixed or user-settable doses of a drug. The drug delivery device 5 may be a pen-type device. The drug delivery device 5 comprises a housing 10, which can be formed from a single or from multiple pieces.

In the embodiment shown in FIG. 1, the housing 10 is attached to a cartridge holder 14, wherein a cartridge 16 containing a medical product or drug can be located. The cartridge holder 14 may be secured against movement with respect to the housing 10.

A needle unit 24 is located at the distal end 22 of the drug delivery device 5 and includes a needle 34. Through the needle 34 of the needle unit 24 the medical product can be injected into a patient. The needle unit 20 can be secured to a needle holder 20 by a threaded engagement. The needle holder 20 forms a part of the cartridge holder 14, for example.

Delivery of the medical product can be performed by means of a piston rod 26, which can be moved into the distal direction towards the distal end 22 with respect to the cartridge 16. A piston 28 is retained in the cartridge 16 and seals the cartridge on the side facing the proximal end 30. The piston 28 can be moved in the distal direction 22 with respect to the cartridge by the piston rod 24. The cartridge holder 14 is fabricated from a transparent, partially transparent or translucent material, so as to allow a user to view the position of the piston 28 within the cartridge 16. In particular, the cartridge holder 14 comprises one single transparent, partially transparent or translucent material.

The piston rod 26 can be expediently connected to a drive mechanism (not explicitly shown), e.g. a mechanical or electrical drive mechanism, and to a dose setting mechanism (not explicitly shown). Drive mechanism and dose setting mechanism are configured to set a dose of the medical product and to move the piston 28 in the distal direction such that the set dose is dispensed from the cartridge 16 when a dispense button of the drug delivery device 5 is pressed.

Piston rod 26 may be engaged in a threaded manner with a lead screw nut (not explicitly shown in FIG. 1), so as to allow a rotationally movable piston rod 26. During operation of the device, the lead screw nut is secured against rotational movement with respect to the housing 10 by a lock nut which may engage into the lead screw nut. Accordingly, the piston rod 26 may rotate and translate with respect to the housing 10, when driven in the distal direction.

It is, however, also conceivable that a linearly movable piston rod is employed. In general, the embodiments of the invention are not restricted to a specific configuration of the piston rod, drive mechanism or dose setting mechanism.

As shown in FIG. 1, the housing 10 includes a window aperture 40. Alternatively or additionally, the window aperture may be provided in the cartridge holder. The housing 10 or the cartridge holder may include two window apertures 40 (not explicitly shown). The two window apertures 40 may be arranged axially offset from each other. The two window apertures 40 may be oppositely disposed. Through the at least one window aperture 40, information attached to the piston rod 26 can be viewed by a user. The window aperture 40 is formed in the embodiment shown in FIG. 1 as a slit. However, other forms of the window aperture 40 are conceivable as well, for example rectangular windows or any other suitable configuration which is known to a person skilled in the art.

According to the embodiment depicted in FIG. 1, information on the piston rod 26 is provided as a plurality of symbols 32. The plurality of symbols 32 comprises consecutive numbers so as to indicate delivered dose or remaining dose left in the cartridge. The symbols 32 can be printed or moulded on the piston rod 26, for example.

In addition, the cartridge holder 14 can include additional information suitable for providing further information to a user. This can be achieved by a label which is wrapped around the cartridge holder 14 (not shown in FIG. 1). The additional information may be visible through the other one of the two window apertures 40.

According to the embodiment shown in FIG. 1, the window aperture 40 is located near the proximal end of the cartridge 16. For example, the window aperture 40 can be located in close proximity to the cartridge holder 14.

According to one embodiment, the side wall of the cartridge holder 14 may comprise an opaque part, in particular a part configured such that the piston rod 26 may not be visible through the side wall of the cartridge holder 14, e.g. a part of the side wall comprising the structured surface. Furthermore, the side wall of the cartridge holder 14 may comprise at least one window aperture, e.g. a part of the side wall of the cartridge holder 14 which does not comprise the structured surface. In particular, the cartridge holder 14 and the housing 10 may be formed unitarily. Through the at least one window aperture the piston rod 26 may be visible. The arrangement of the symbols 32 on the piston rod 26 may be chosen such that they are covered by the opaque part of the side wall of the cartridge holder 14. But nevertheless, the symbols 32 may be displayed through the window aperture in the housing or an (additional) window aperture in the cartridge holder 14, which is angularly offset from the previously mentioned window aperture. The (additional) window aperture for displaying the symbols 32 on the piston rod 26 is expediently arranged in the proximal end section of the cartridge holder 14.

When the drug contained in the cartridge 16 is dispensed from the drug delivery device 5, the piston 28 advances towards the distal end 22 of the cartridge 16. Through the window aperture 40 in the housing 10 and/or in the side wall of the cartridge holder 14, at least a one of the numbers of the plurality of symbols 32 on the piston rod 26 is framed by the window aperture 40. It is also conceivable that more than one, e.g. two symbols 32 are visible at once.

Making now reference to FIG. 2, the distal end of the piston rod 26 is shown in more detail. In the embodiment shown in FIG. 2, the piston rod 26 is constructed as a rotationally movable piston rod, as indicated by a helically shaped surface. On the piston rod 26, symbols 32 are located so as to provide dosage information.

As mentioned above, the cartridge holder 14 includes an at least partially transparent side wall. According to an embodiment, the side wall comprises a structured surface so as to be capable of unevenly reflecting or refracting light which renders the symbols 32 of the piston rod 26 at least partially unreadable.

During operation, the piston 28 and the piston rod 26 progressively advance towards the distal end 22 of the cartridge 16. In order to make the symbols 32 on the piston rod 26 unreadable through the cartridge holder 14, the structured surface is employed. The structured surface of the side wall can be arranged on the inner surface 34 of the cartridge holder 14, for example.

The structured surface of the at least partially transparent side wall includes structural elements, which can be formed as facets or undulating elements, for example.

Making now reference to FIG. 3A, the inner surface 34 of the cartridge holder 14 is shown in more detail. In the embodiment shown in FIG. 3A, the structural elements 42 are formed as facets which extend inwardly from the inner surface 36 of the cartridge holder 14. It should be noted that the structural elements 42 can also be formed as grooves in the inner surface 36 of the cartridge holder 14. The structural elements 42 can be orientated along a horizontal axis between the proximal end 30 and the distal end 22 as parallel line shaped elements.

Making now reference to FIG. 3B, the effect of the structured surface is depicted. FIG. 3B shows a detailed view of one symbol 32, when viewed through the side wall of the cartridge holder 14. Due to an unevenly reflecting or refracting behaviour, the symbol 32 on the piston rod 26 is at least partially unreadable.

Making now reference to FIG. 4, the distal part of the drug delivery device is shown in more detail. According to the embodiment depicted in FIG. 4 the piston 28 is advanced to some extend into the cartridge 16. As shown in FIG. 4, the structured surface of the cartridge holder 14 is capable of retaining the piston 28 visible during engagement in the cartridge 16.

In the embodiment of FIG. 4, the structural elements 42 are orientated horizontally between the proximal end 30 and the distal end 22 as parallel oriented facets. According to the embodiment of FIG. 4, the end face of the piston 28 is arranged perpendicular to the axis of the facets, which allows viewing the position of the piston 26.

Other implementations are within the scope of the following claims. Elements of different implementations may be combined to form implementations not specifically described herein.

| Reference numerals | |
|---|---|
| Drug delivery device | 5 |
| Housing | 10 |
| Cartridge holder | 14 |
| Cartridge | 16 |
| Needle holder | 20 |
| Distal end | 22 |
| Needle unit | 24 |
| Piston rod | 26 |
| Piston | 28 |
| Proximal end | 30 |
| Symbols | 32 |
| Needle | 34 |
| Inner surface | 36 |
| Window aperture | 40 |
| Structural element | 42 |

The invention claimed is:

1. A drug delivery device comprising:
   a housing with a proximal end and a distal end,
   a cartridge holder adapted to retain a cartridge, the cartridge holder comprising an at least partially transparent side wall,
   a piston rod, the piston rod being adapted to drive a piston so as to engage the piston into the cartridge, and
   a plurality of symbols on the piston rod, the symbols representing dosage information during operation of the drug delivery device and being visible through a window aperture in the housing or in the cartridge holder
   wherein a filling status of the drug delivery device is recognizable by viewing at least one of the symbols on the piston rod through the window aperture
   wherein only one symbol is viewed through the window aperture at a time on the piston rod and this particular viewed symbol represents an amount of medicinal product delivered
   wherein the at least partially transparent side wall of the cartridge holder comprises a plurality of structural elements located on an inner surface of the side wall, the structural elements being transparent and being capable of unevenly reflecting light so as to at least partially render the symbols of the piston rod unreadable, wherein the structural elements comprise facets, undulating elements, or grooves.

2. The drug delivery device according to claim 1, wherein the structural elements of the at least partially transparent side wall are capable of retaining the piston visible during engagement in the cartridge.

3. The drug delivery device according to claim 1, wherein the structural elements of the at least partially transparent side wall comprise features being orientated along a horizontal axis between the proximal end and the distal end.

4. The drug delivery device according to claim 1, wherein the plurality of symbols comprises consecutive numbers so as to indicate delivered dose or remaining dose left in the cartridge.

5. The drug delivery device according to claim 4, wherein the numbers are printed or moulded on the piston rod.

6. The drug delivery device according to claim 1, wherein the cartridge holder comprises additional information suitable for providing further information to a user.

7. The drug delivery device according to claim 1, wherein the piston rod is a linearly movable piston rod.

8. The drug delivery device according to claim 1, wherein the piston rod is a rotationally movable piston rod.

9. The drug delivery device according to claim 1, wherein the structural elements of the at least partially transparent side wall cover the upper part of the cartridge holder facing the proximal end.

10. The drug delivery device according to claim 1, wherein the cartridge holder retains the cartridge and the window aperture is located above the proximal end of the cartridge.

11. The drug delivery device according to claim 10, wherein the aperture is located in close proximity to the cartridge holder.

12. The drug delivery device according to claim 1, wherein the side wall of the cartridge holder comprises an opaque part as well as at least one window aperture through which the piston rod is visible, wherein the piston rod is not rotated as it drives the piston and wherein the arrangement of the symbols is chosen such that they are covered by the opaque part of the side wall of the cartridge holder.

13. The drug delivery device according to claim 12, wherein the symbols are arranged linearly on the piston rod.

14. The drug delivery device according to claim 12, wherein regarding the longitudinal axis of the piston rod the angular position of the window aperture of side wall of the cartridge holder is offset with respect to the angular position of the window aperture in the housing.

15. The drug delivery device according to claim 14, wherein the angular offset is defined in a range between 80 degree and 100 degree.

16. A drug delivery device comprising:
a housing with a proximal end and a distal end,
a cartridge holder adapted to retain a cartridge, the cartridge holder comprising an at least partially transparent side wall,
a piston rod, the piston rod being adapted to drive a piston of a cartridge retained within the cartridge holder, so as to drive the piston into the cartridge, and
a plurality of symbols on the piston rod, the symbols representing dosage information during operation of the drug delivery device
wherein only one symbol is visible at a time through a window aperture in the housing or in the cartridge holder
wherein the symbols indicate a delivered amount of medicinal product or a remaining amount of medicinal product contained within the cartridge
wherein the at least partially transparent side wall of the cartridge holder comprises a plurality of structural elements located on an inner surface of the side wall, the structural elements being transparent and being capable of unevenly reflecting light so as to at least partially render the symbols of the piston rod unreadable, wherein the structural elements comprise facets, undulating elements, or grooves.

17. A drug delivery device comprising:
a housing with a proximal end and a distal end,
a cartridge holder adapted to retain a cartridge, the cartridge holder comprising an at least partially transparent side wall,
a piston rod, the piston rod being adapted to drive a piston so as to engage the piston into the cartridge, and
a plurality of symbols on the piston rod, the symbols representing dosage information during operation of the drug delivery device and being visible through a window aperture in the housing or in the cartridge holder
wherein a filling status of the drug delivery device is recognizable by viewing at least one of the symbols on the piston rod through the window aperture
wherein only one symbol is viewed through the window aperture at a time on the piston rod and this particular viewed symbol represents a remaining amount of medicinal product contained within the cartridge
wherein the at least partially transparent side wall of the cartridge holder comprises a plurality of structural elements located on an inner surface of the side wall, the structural elements being transparent and being capable of unevenly reflecting light so as to at least partially render the symbols of the piston rod unreadable, wherein the structural elements comprise facets, undulating elements, or grooves.

* * * * *